(12) United States Patent
Halwani et al.

(10) Patent No.: US 9,931,056 B2
(45) Date of Patent: Apr. 3, 2018

(54) SPIROMETER BREATHING TUBE WITH COMPOUND MEMBRANE

(75) Inventors: Fouad Halwani, Kirkland (CA); Nathan Ayoubi, Vancouver (CA); Jose Ganseman, Denderleeuw (BE); Judy Findlay, Vancouver (CA); Thomas Lloyd Bellaire, Burnaby (CA); Ian Brodkin, Vancouver (CA); Arthur Willms, Surrey (CA); Victor Dosil, Delta (CA); Awni Ayoubi, Surrey (CA)

(73) Assignee: Rostrum Medical Innovations Inc. (CA)

( * ) Notice: Subject to any disclaimer, the term of this patent is extended or adjusted under 35 U.S.C. 154(b) by 858 days.

(21) Appl. No.: 13/807,240

(22) PCT Filed: Jun. 29, 2011

(86) PCT No.: PCT/CA2011/000774
§ 371 (c)(1),
(2), (4) Date: Mar. 14, 2013

(87) PCT Pub. No.: WO2012/000101
PCT Pub. Date: Jan. 5, 2012

(65) Prior Publication Data
US 2013/0172773 A1     Jul. 4, 2013

Related U.S. Application Data

(60) Provisional application No. 61/359,771, filed on Jun. 29, 2010.

(51) Int. Cl.
*A61B 5/08*     (2006.01)
*A61B 5/087*     (2006.01)

(52) U.S. Cl.
CPC .................. *A61B 5/0876* (2013.01)

(58) Field of Classification Search
USPC ........ 600/538; 128/203.12; 137/561; 29/592
See application file for complete search history.

(56) References Cited

U.S. PATENT DOCUMENTS 3,237,846 A * 3/1966 Brown .................. A47L 9/1454
                                                                   383/61.1
3,389,519 A * 6/1968 Williams ................ E04C 2/296
                                                                    264/46.5

(Continued)

FOREIGN PATENT DOCUMENTS

| FR | 2360063 | 2/1978 |
|---|---|---|
| WO | WO2008/106961 | 9/2008 |
| WO | WO 2008106961 | 9/2008 |

OTHER PUBLICATIONS

Extended European Search Report for EP Application No. 11800025.6, dated Feb. 11, 2013, 4 pages.

(Continued)

*Primary Examiner* — Christian Jang
*Assistant Examiner* — Mitchell E Alter
(74) *Attorney, Agent, or Firm* — Klarquist Sparkman, LLP

(57) ABSTRACT

A compound membrane breathing tube for use in spirometric applications is provided. The compound membrane comprises a first sheet and a second sheet of flexible sheeting connected together along the periphery thereof, and each of the sheets has an opening cut therethrough to create a flap. The flap of the first sheet overlaps the flap of the second sheet so as to present a higher relative resistance to airflow through the breathing tube at lower airflows.

13 Claims, 5 Drawing Sheets

(56) References Cited

U.S. PATENT DOCUMENTS

| | | | | |
|---|---|---|---|---|
| 3,467,078 | A * | 9/1969 | Bird | A61B 5/091 |
| | | | | 128/204.25 |
| 3,726,436 | A * | 4/1973 | Despain | B65D 47/2031 |
| | | | | 222/213 |
| 4,391,283 | A * | 7/1983 | Sharpless | A61B 5/0875 |
| | | | | 482/13 |
| 4,706,685 | A * | 11/1987 | Jones, Jr. | A61B 5/0935 |
| | | | | 600/538 |
| 5,355,910 | A * | 10/1994 | Gies | B60H 1/249 |
| | | | | 137/855 |
| 5,979,247 | A | 11/1999 | Kizawa | |
| 6,066,101 | A * | 5/2000 | Johnson | A61B 5/087 |
| | | | | 600/529 |
| 2003/0097880 | A1 * | 5/2003 | Ciobanu | G01F 1/42 |
| | | | | 73/861.52 |
| 2007/0071880 | A1 * | 3/2007 | Simon | A61L 2/08 |
| | | | | 427/8 |
| 2008/0077038 | A1 | 3/2008 | McDonough et al. | |
| 2009/0145441 | A1 * | 6/2009 | Doshi | A61M 15/08 |
| | | | | 128/207.18 |

OTHER PUBLICATIONS

Patent Examination Report No. 1 for AU Application No. 2011274212, dated Apr. 12, 2013, 2 pages.
International Search Report for PCT/CA2011/000774, dated Sep. 22, 2011.

\* cited by examiner

US 9,931,056 B2

SPIROMETER BREATHING TUBE WITH COMPOUND MEMBRANE

CROSS-REFERENCE TO RELATED APPLICATION

This is the U.S. National Stage of International Application No. PCT/CA2011/000774, filed Jun. 29, 2011, which was published in English under PCT Article 21(2), which in turn claims priority to and the benefit of U.S. Provisional Application No. 61/359,771, filed Jun. 29, 2010. The provisional application is incorporated herein by reference in its entirety.

FIELD

The presently disclosed subject matter relates to methods and apparatus employed in the measurement of inspired and expired airflows from a patient undergoing spirometric evaluation.

BACKGROUND

Numerous devices, usually referred to as spirometers, have been developed to measure and monitor the breathing flow rates in human subjects. Conventional spirometers are typically used in conjunction with a breathing tube through which the inspired and expired airflows travel, and which is preferably disposable in order to minimize the risks of cross-contamination. A variety of active elements such as turbines, calibrated orifices, pitot tubes, venturis and resistive membranes are typically placed in the spirometer breathing tube in order to enable the measurement of the flow rate of the air travelling therethrough.

SUMMARY

The presently disclosed and claimed subject matter provides a breathing tube and compound membrane for use in spirometric applications. The compound membrane creates pressure differentials across the breathing tube that are used by the spirometric measuring device to compute airflows, and comprises a first sheet and a second sheet of flexible sheeting connected together along the periphery thereof. Each of the first and second sheets comprises an opening cut therethrough to create a flap, and the flap of the first sheet overlaps the flap of the second sheet so as to present a higher relative resistance to airflow through the breathing tube at lower airflows when membrane overlap is relatively high.

The breathing tube is preferably disposable, and preferably includes locking breakaway lugs to facilitate precise alignment and locking of the breathing tube to a spirometric measuring device, and to discourage re-use of the breathing tube after removal.

BRIEF DESCRIPTION OF THE DRAWINGS

For a fuller understanding of the nature and advantages of the disclosed subject matter, as well as the preferred mode of use thereof, reference should be made to the following detailed description, read in conjunction with the accompanying drawings. In the following drawings, like reference numerals designate like or similar parts or steps.

DETAILED DESCRIPTION

Figure 1A:
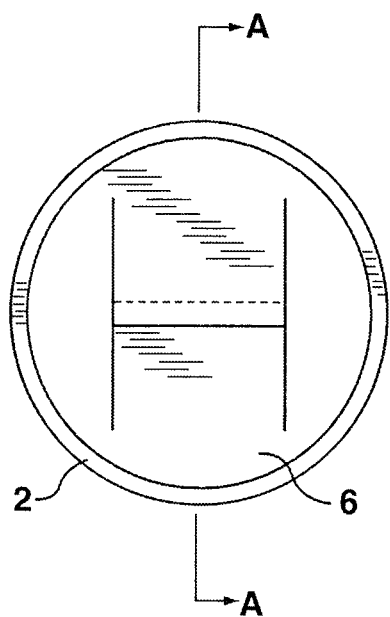
FIG. 1A is a schematic end view of a breathing tube in accordance with an embodiment of the disclosed subject matter.
Figure 1B:
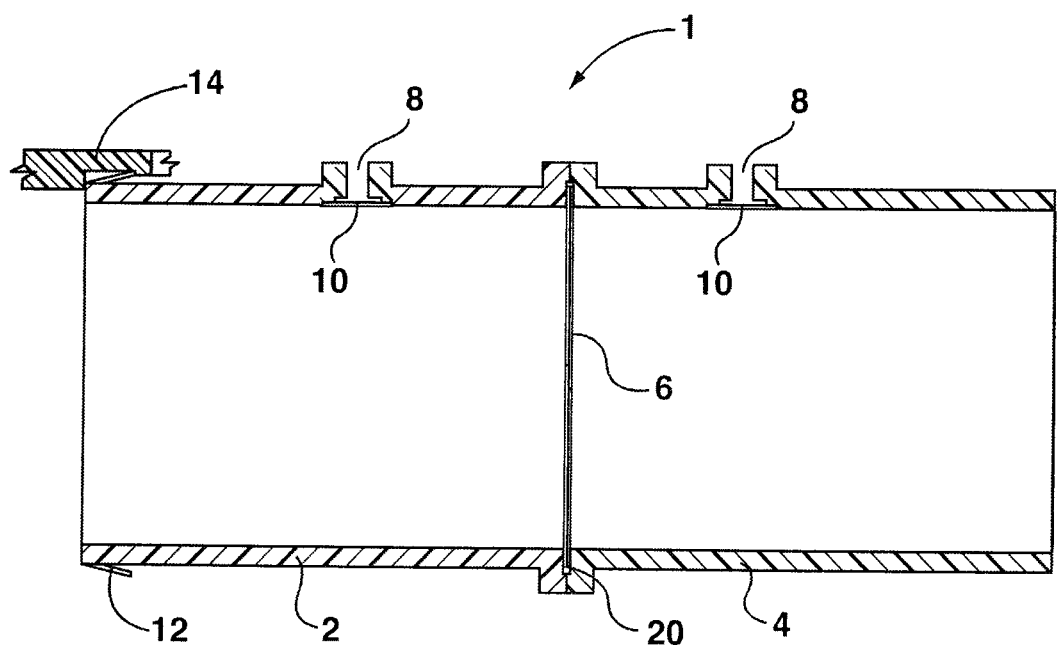
FIG. 1B is a schematic cross-sectional view of the breathing tube of FIG. 1A, taken along line A-A.

Referring to FIGS. 1A and 1B, breathing tube 1 generally comprises two tubular sections 2 and 4 connected in end-to-end relationship. In typical applications, each of tubular sections 2 and 4 are constructed of a rigid (preferably transparent plastic) material, and are connected together in a conventional manner such as by gluing or welding. Sandwiched between tubular sections 2 and 4 is compound membrane 6, which comprises two pieces of flexible sheeting. Sections 2 and 4 each further comprise a pressure tapping outlet 8 for fluid connection to a spirometric measuring device 14, and in preferred embodiments each tapping outlet 8 is covered by a filtering membrane 10 to reduce the likelihood of cross-contamination. Filtering membrane 10 is typically much larger than the cross sectional area of the tapping outlet 8.

The free end of at least section 2 may include locking breakaway lugs 12 to facilitate precise alignment and locking of the breathing tube 1 to a spirometric measuring device 14. Upon removal of the breathing tube 1 (such as after the completion of a test sequence), lugs 12 break off of the breathing tube 1 without damaging the measuring device 14. This discourages any attempt to re-use breathing tube 1.

Figure 2A:
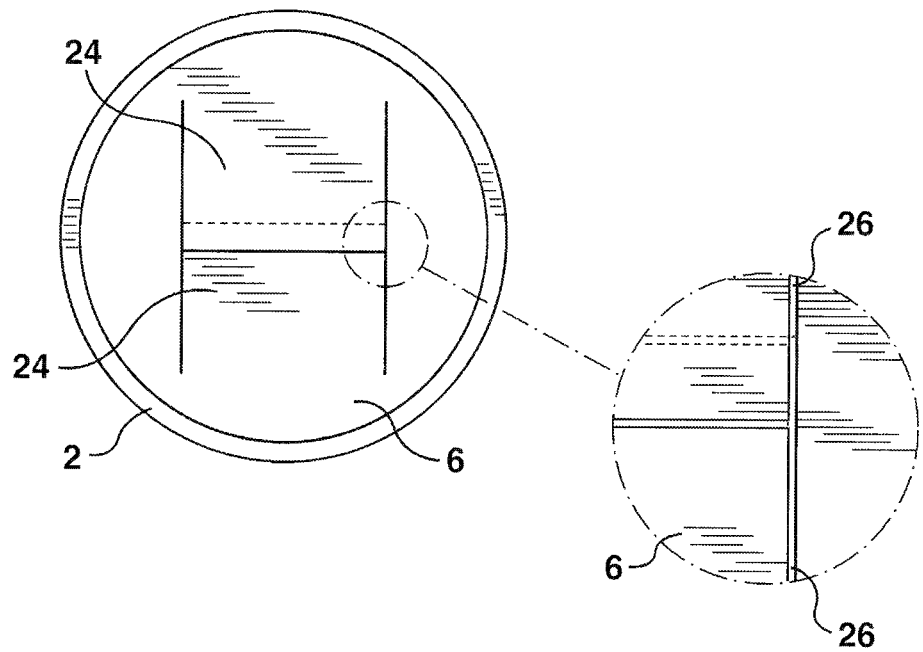
FIG. 2A is an enlarged schematic end view of the membrane of the breathing tube of FIG. 1A.
Figure 2B:
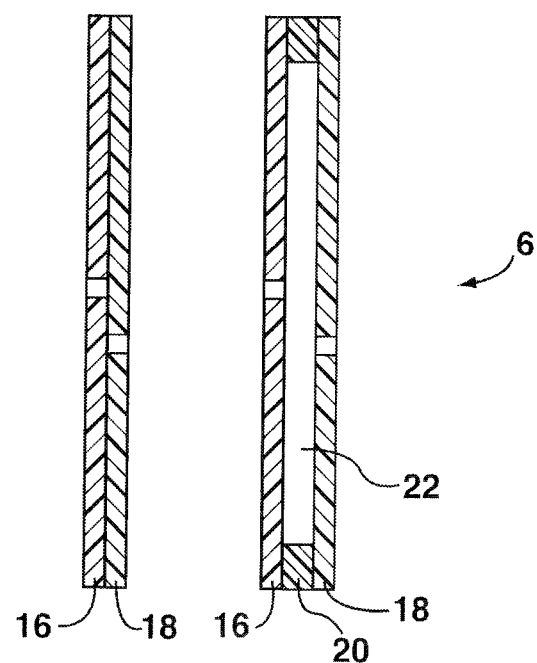
FIG. 2B is an enlarged cross-sectional side elevation of the membrane of the breathing tube of FIG. 1A.
Figure 2C:
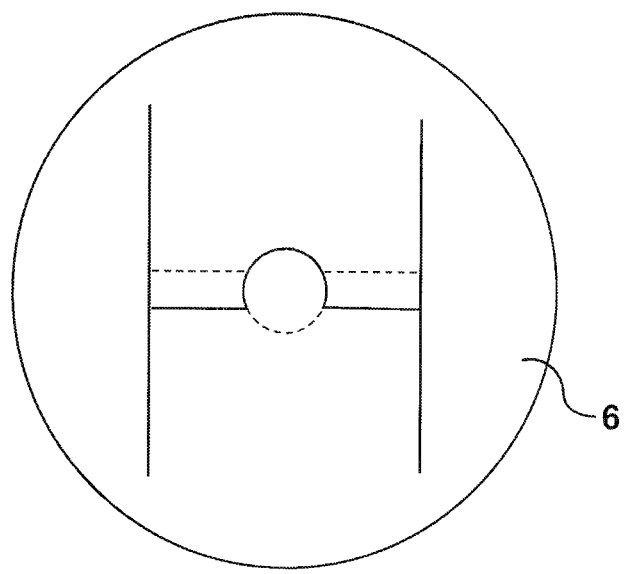
FIG. 2C is a schematic end view of the membrane a breathing tube in accordance with an alternative embodiment of the disclosed subject matter.

FIGS. 2A and 2B illustrate in enlarged end elevational and cross-sectional views the central portion of compound membrane 6. Front sheet 16 and back sheet 18 of compound membrane 6 may be directly connected together along their periphery such as by gluing or welding, or may be separated by a peripheral ring-spacer 20 to create a variable gap 22 between the sheets depending on the thickness of ring-spacer 20. Each of the membrane sheets 16 and 18 is cut using a precision apparatus such as a laser cutter to create a flap 24. Ideally, the gap 26 created by the cutter along the margins of each flap 24 has a constant width and is kept within very tight tolerances.

The two flaps 24 (one in membrane sheet 16 and the other in membrane sheet 18) overlap along at least a portion thereof, and the overlapped area, along with the gap 22 (if any) between the sheets can be varied in order to modify the response of a particular compound membrane design to the airflow through a particular breathing tube 1. The shape of flaps 24 is also variable, and may include polygonal or curved shapes and/or openings as illustrated by way of example in FIGS. 2C, 3 and 5A-5L. The thickness and flexural rigidity of the sheets 16 and 18 can also be varied together or separately. Yet other variations are possible, and the only conserved feature of the compound membrane 6 is the presence of an overlap between the flaps 24 cut into the two sheets 16 and 18.

Figure 4:
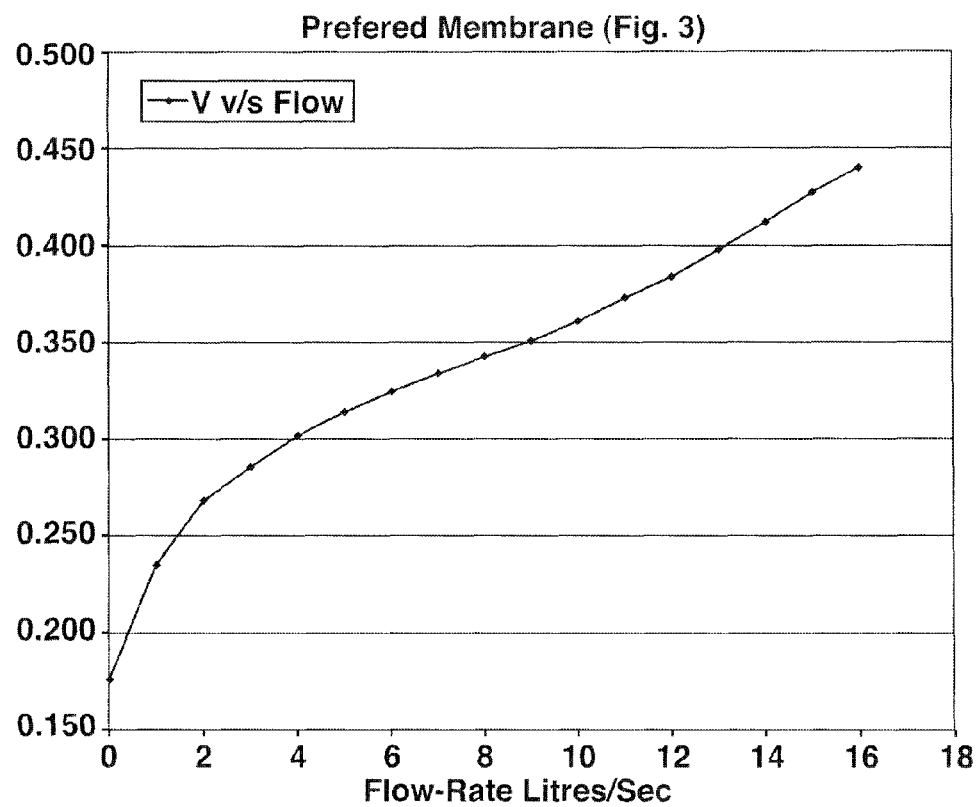
FIG. 4 is a graph illustrating a typical voltage vs. airflow response curve for the breathing tube membrane of FIG. 3.
Figures 5A, 5B, 5C, 5D, 5E, 5F, 5G, 5H, 5I, 5J, 5K, 5L:
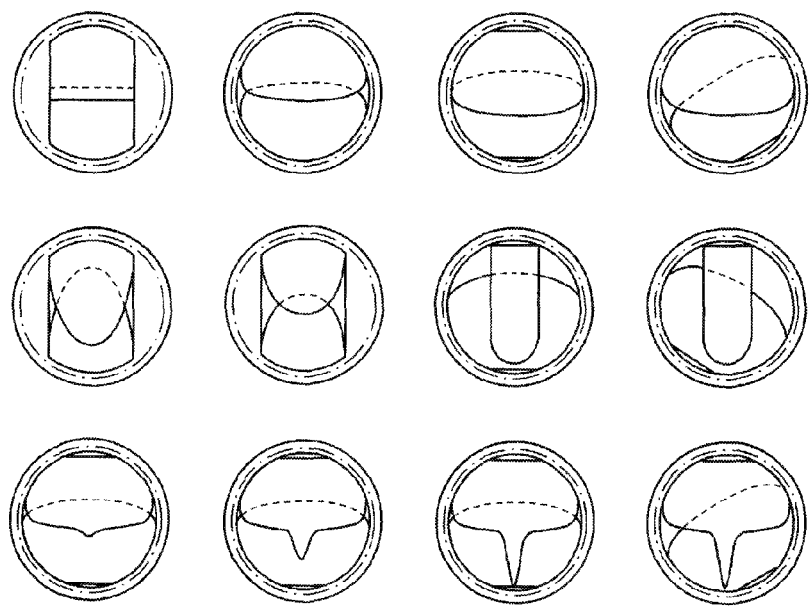
FIGS. 5A-5L are schematic end views of breathing tubes in accordance with further alternative embodiments of the disclosed subject matter; and, FIG. 6 is an enlarged cross-sectional side elevation of a breathing tube membrane in accordance with alternative embodiments of the disclosed subject matter.

The overlap between the flaps 24 will typically present a higher relative resistance at lower airflows when membrane overlap is high. This relative resistance drops as the airflow through breathing tube 1 increases and the overlap between the sheet flaps is reduced or disappears altogether (as the flaps 24 are deflected by the airflow through the breathing tube 1). As seen in FIG. 4, the voltage vs. airflow response curve generated when a breathing tube 1 is used in a spirometric application is non-linear, typically exhibiting a steeper slope at low airflows and tapering off at higher airflows. This permits less variation in measurement precision over the full airflow range typically experienced in a breathing tube 1. In prior known devices, the voltage vs. airflow response curve tends to be linear at best or inverted at worst (i.e. resistance starts low then increases exponentially with flow).

The presently described compound membrane design also readily allows airflow resistance to be optimally modulated for different applications (e.g. children, respiratory deficient patients, Operating Room ventilation devices, etc.), by modifying membrane geometries, membrane orientations and/or working diameters depending on the application.

Figure 3:
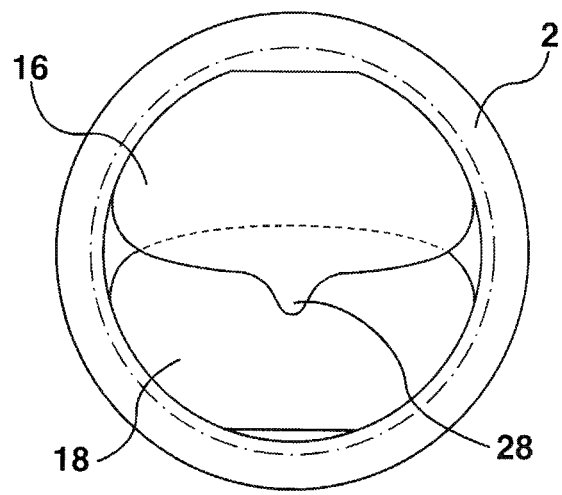
FIG. 3 is a schematic end view of a breathing tube in accordance with a preferred alternative embodiment of the disclosed subject matter.

FIG. 3 illustrates a preferred embodiment of membrane 6 in which the flap 24 of front sheet 16 includes a protrusion or "finger" 28 to lessen the risk of jamming of the membrane 6 under working conditions (when the flaps 24 are deflected by the airflow through the breathing tube 1). FIG. 4 illustrates a typical voltage vs. airflow response curve for a breathing tube 1 that has a membrane 6 of this configuration.

Figure 6:
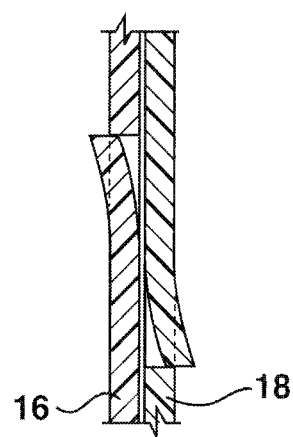

FIGS. 5A-5L illustrate further exemplary alternative embodiments of membrane 6, and FIG. 6 shows a further optional molding of the tips of flaps 24 into a curl to reduce further the risk of jamming during use.

The present description includes the best presently contemplated mode of carrying out the subject matter disclosed and claimed herein, and is made for the purpose of illustrating the general principles of the subject matter and not be taken in a limiting sense; the subject matter can find utility in a variety of implementations without departing from the scope of the disclosure made, as will be apparent to those of skill in the art from an understanding of the principles that underlie the subject matter.

We claim:

1. A spirometer breathing tube comprising:
a first tubular section and a second tubular section connected together in end-to-end relationship to secure a compound membrane in a generally perpendicular orientation therebetween, wherein the compound membrane comprises a first sheet of flexible sheeting and a second sheet of flexible sheeting connected together along a periphery thereof, wherein each of said first and second sheets defines a respective opening therethrough configured as a respective flap, and wherein the flap of the first sheet overlaps the flap of the second sheet.

2. The spirometer breathing tube of claim 1, wherein the flap of at least one of said first sheet and said second sheet comprises a protrusion defining a zone of extended overlap relative to the flap of the other one of the first and second sheets.

3. A method of using the spirometer breathing tube of claim 1 in a spirometric evaluation, the method comprising:
attaching the spirometer breathing tube to a spirometric measuring device, and
measuring a flow rate of air travelling through the spirometer breathing tube.

4. The spirometer breathing tube of claim 1, wherein the peripheries of the first and second sheets are bonded together.

5. The spirometer breathing tube of claim 1, further comprising a peripheral spacer between the respective peripheries of the first and second sheets.

6. The spirometer breathing tube of claim 5, wherein the peripheral spacer defines a variable gap between the first and second sheets, the gap being defined by a thickness of the peripheral spacer.

7. The method of claim 3, wherein the act of attaching the spirometer breathing tube to a spirometric measuring device comprises attaching the spirometer breathing tube using breakaway lugs.

8. The spirometer breathing tube of claim 1, further comprising breakaway lugs for attaching the breathing tube to a spirometric measuring device.

9. A method of manufacturing the compound membrane of claim 1, comprising connecting a front sheet and a back sheet of the compound membrane along their peripheries, wherein the flap in the front sheet and the flap in the back sheet overlap along at least a portion thereof.

10. The method of claim 9, comprising cutting each of the membrane sheets using a laser cutter to create the flaps.

11. The method of claim 10, wherein a gap created by the cutter along the margins of each flap has a constant width.

12. The method of claim 9, wherein the membrane sheets are directly connected together by gluing or welding.

13. The method of claim 9, wherein a peripheral ring-spacer creates a variable gap between the membrane sheets.

* * * * *